United States Patent [19]

Manciocchi, Jr.

[11] Patent Number: 4,509,541

[45] Date of Patent: Apr. 9, 1985

[54] ANTISEPTIC TOOTHPICK

[75] Inventor: William D. Manciocchi, Jr., 803 Diamond St., Williamsport, Pa. 17701

[73] Assignees: William D. Manciocchi, Jr.; Lawrence S. Allison; Robert F. Griffin, Jr.; Steven J. Hall, all of Williamsport, Pa.

[21] Appl. No.: 507,745

[22] Filed: Jun. 24, 1983

[51] Int. Cl.³ .................... A61C 15/00; B43K 5/16
[52] U.S. Cl. .................................. 132/90; 401/116
[58] Field of Search .............. 132/89, 90, 93, 88.5, 132/88.7, DIG. 3; 401/109, 99, 111, 115, 116, 117; 604/181, 185, 187

[56] References Cited

U.S. PATENT DOCUMENTS

| | | | |
|---|---|---|---|
| 2,931,370 | 4/1960 | Jackson | 132/89 |
| 3,428,404 | 2/1969 | Cianco | 401/109 |
| 4,019,522 | 4/1977 | Elbreder | 132/90 |
| 4,040,433 | 8/1977 | Edison | 132/89 |
| 4,231,381 | 11/1980 | Battista | 132/89 |

FOREIGN PATENT DOCUMENTS 2452277  11/1980  France ........................ 132/90

Primary Examiner—Richard J. Apley
Assistant Examiner—Carolyn A. Harrison
Attorney, Agent, or Firm—Ruth Moyerman

[57] ABSTRACT

An antiseptic toothpick is disclosed. A case contains a hollow cylinder. The cylinder and case are threadably engaged to give controllable telescopic action. The hollow cylinder is capable of containing antiseptic liquid and has a wick at its top. A toothpick is fastened to the inside base end of the case and extends longitudinally into and through said hollow cylinder, its liquid and its wick. Through telescopic action, the hollow cylinder is retracted into the case, exposing the toothpick for use. When the telescoping action is reversed, the wick may be used to clean teeth and gums with the antiseptic liquid because the toothpick is retracted.

12 Claims, 4 Drawing Figures

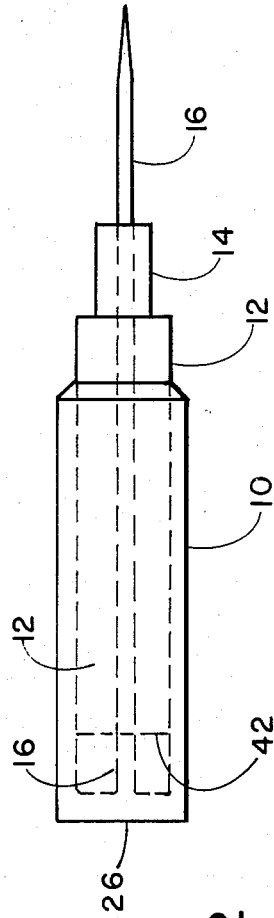
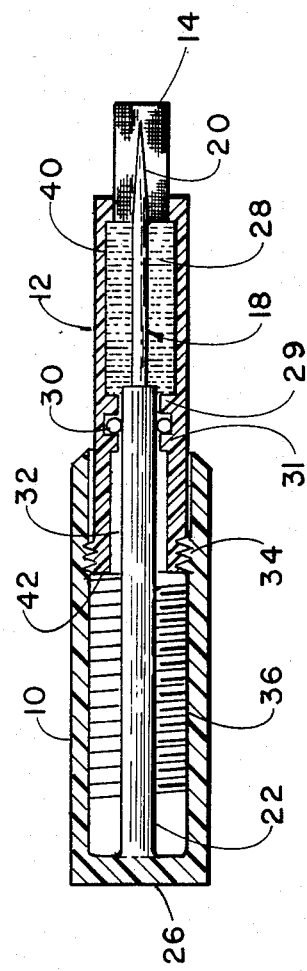
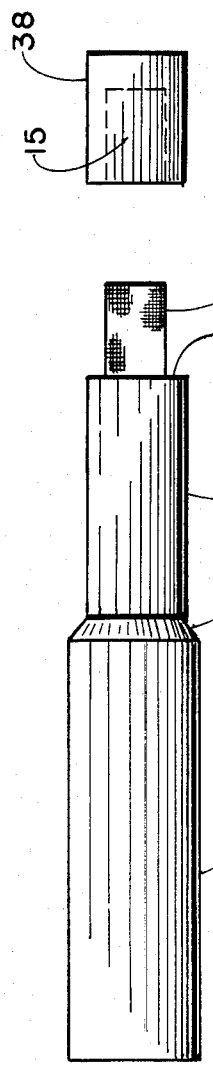
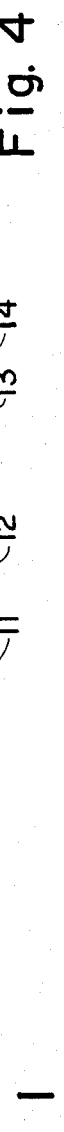
Fig. 2
Fig. 3
Fig. 4
Fig. 1

ANTISEPTIC TOOTHPICK

BACKGROUND OF THE INVENTION

1. Field of the Invention

This invention relates to toothpicks and more particularly to a special receptacle for a toothpick.

2. Description of the Prior Art

Today there is a great emphasis on dental care and especially on preventive dental care. A good many devices have been proposed to facilitate cleansing of teeth and prevention of decay by control of bacterial growth in the mouth.

U.S. Pat. No. 410,794 to Hellwig discloses a disinfectant toothpick made by soaking wooden toothpicks in a disinfectant solution before use. The toothpicks are each used once and then discarded. The disinfectant is in a non-sealed container.

U.S. Pat. No. 4,040,433 to Edison discloses a reusable toothpick stored in a vial into which mouthwash may be placed. The toothpick is cleansed after each use by placing it in the vial.

U.S. Pat. No. 4,231,381 to Battista discloses a throwaway dental aid which includes a bottle of mouthwash and a toothpick attached to the bottle cap so that the toothpick is encapsulated in the bottle.

None of the above devices provides for the application of an antiseptic solution to the teeth and gums. No device is known which provides simultaneously for mechanical cleansing of teeth with a toothpick as well as application of antiseptic to the teeth and gums.

There is, therefore, a great need for a device which will cleanse the teeth of food particles with a toothpick and, additionally, apply antiseptic to teeth and gums for eliminating bacteria.

There is also a need for a reusable device which is easily carried on one's person so that preventive dental care need not be confined to the home or a dentist's office.

In addition, there is a need for a nonbreakable, nonspillable device which provides for mechanical and chemical cleansing of teeth and mouth with an easy-to-operate antiseptic toothpick.

SUMMARY OF THE INVENTION

The aforementioned prior art problems are obviated by the device of this invention in which a toothpick is retractably contained in a case which also contains antiseptic liquid and an applicator for the liquid.

The device is preferably cylindrical in shape, having a cap at one end. There is a case threaded internally and an antiseptic-containing cylinder sealed at both ends and threadably engaged to the case to give controllable telescopic action. Centered inside case and cylinder is a toothpick fastened to the inner base of the case and moved retractably through the antiseptic by the telescoping action.

A wick is sealably placed inside the cap end of the antiseptic-containing cylinder so that one end of the wick absorbs the antiseptic and transmits it to the opposite end which extends from the cylinder to form an applicator. Thus, when the toothpick is extended through the wick, it is itself cleansed before each use.

In addition to cleaning teeth cavities with the toothpick, the user may place the wick itself, after the toothpick is retracted, against teeth and gums for antiseptic treatment of the mouth.

It is, therefore, an object of this invention to provide a device for antiseptic cleansing of the teeth and gums.

It is another object of this invention to provide a reusable toothpick.

It is still another object of this invention to provide a device for neat and simple application of antiseptic liquid to teeth and gums.

It is a further object of this invention to provide a truly portable and discreet device for cleaning of teeth away from home or dentist's office.

It is yet a further object of this invention to provide a nonbreakable, nonspillable device containing antiseptic liquid or mouthwash.

These and other objects will be more readily ascertainable to one skilled in the art from a consideration of the Figures and the following description and exemplary embodiment.

BRIEF DESCRIPTION OF THE DRAWING(S)

FIG. 1 is a perspective view of the preferred embodiment of this invention as it would look when the toothpick is retracted.

FIG. 2 is an elevation with the toothpick extended for use and showing an alternate embodiment of the toothpick in phantom.

FIG. 3 is a longitudinal cross section showing the toothpick retracted.

FIG. 4 is an isometric of the cap of this invention, the wick opening shown in phantom.

DETAILED DESCRIPTION OF THE PREFERRED EMBODIMENT(S)

Referring now to the drawings, and more particularly to FIG. 1, the exterior of the invention is shown. An outer case-forming cylinder 10 is shown with second cylinder 12 extending upward from top end 11 of cylindrical case 10. Wick 14 is shown at uppermost end 13 of second cylinder 12. Cylinders 10 and 12 are threadably engaged (shown in FIG. 3) so that cylinder 12 can be telescoped out of top end 11 of cylindrical case 10 into the position shown in FIG. 1. Wick 14 is sealably attached to the exterior top end 13 of cylinder 12 so as to absorb and transmit liquid as will be explained with reference to FIG. 3.

Referring now to FIG. 2, toothpick 16 is shown extending through wick 14, ready for use. Telescopic action has drawn cylinder 12 inward, causing toothpick 16 to protract through wick 14. Cylinder 12, seen also in phantom in its retracted position inside cylindrical case 10, ends in base 42. It can be seen in FIG. 2 that toothpick 16 is stationery, being made available for use by retraction of cylinder 12. FIG. 2 shows an embodiment of the invention where toothpick 16 is one continuous element attached to interior base 26 of case 10.

The interior of the invention is shown in FIG. 3. In this embodiment, toothpick 18 is shown having two sections—a top tapered pin 20 and a lower rod 22. Top tapered pin 20 of toothpick 18 is shown passing through wick 14 into antiseptic liquid 28. Thus, toothpick 18 becomes antiseptic each time it is drawn through antiseptic liquid 28 and wick 14 which is saturated with antiseptic.

Wick 14 is shown in FIG. 3 extending into antiseptic 28. Wick 14 absorbs antiseptic liquid 28. Thus, the user may apply antiseptic to his teeth and gums using wick 14 as an applicator when cylinder 12 is protracted from cylinder 10, thereby covering toothpick 18. It may be seen that wick 14 sufficiently surrounds and pads the point of toothpick pin 20 so that the user will not be pricked by toothpick pin 20 when he is applying antiseptic in wick 14 to his teeth and gums.

FIG. 3 also shows rod 22 of toothpick 18 joining tapered pin 20 inside chamber 40. Chamber 40 is formed by interior walls of cylider 12 and contains antiseptic liquid 28. Rod 22 of toothpick 18 extends downward from inside chamber 40, through upper shoulders 29, sealing means 30, lower shoulders 31, through base 42 of cylinder 12 and through chamber 32 of cylinder 10, to be attached to interior center of base 26 of cylinder 10. Sealing means 30 is shown as an O-ring but any gasket or sealer which prevents seepage of antiseptic liquid 28 out of chamber 40 is acceptable.

The telescoping action of this invention is also shown in FIG. 3. Chamber 32, formed by the interior walls of cylindrical case 10, allows room for cylinder 12 when cylinder 12 is retracted. Although case 10 is shown as cylindrical, any exterior shape with cylindrical interior walls is possible. Threads 34 on the exterior walls of cylinder 12 engage threads 36 on the interior walls of cylindrical case 10. As threads 34 and 36 engage, cylinder 12 is moved in and out of cylindrical case 10, making either toothpick 18 or wick 14 available for use.

Now referring to FIG. 4, cap 38 is shown with wick opening 15 shown in phantom. Cap 38 prevents wick 14 from drying out when wick 14 or toothpick 18 is not being used. Cap 38 also keeps wick 14 from possible contamination.

There are many variations which may be practiced within the scope of this invention. For example, the toothpick may be two-part as described in FIG. 3, or one part as indicated in phantom in FIG. 2.

The exterior of the case may be any shape as long as its interior walls are capable of becoming threadably engaged to the hollow cylinder.

The cap is optional, although preferred. Gasket or O-rings are specified to seal antiseptic liquid 28 into chamber 40 at lower end of chamber 40. Any sealer may be employed which will prevent seepage of antiseptic liquid 28.

All parts of case 10 and cylinder 12 may be plastic, as may cap 38. Toothpick 18 may be plastic, hard rubber, or any fine, rigid material. The overall dimensions of the antiseptic toothpick are not critical, but are conveniently of a size to fit unobtrusively in a pocket or handbag.

Also, antiseptic liquid is mentioned, but a mouthwash or mouth freshener or fluoride may be used and still be within the scope of this invention.

Wick 14 is preferably felt, but any absorbent material may be used.

The device of this invention has many advantages. Chiefly among these is that the device provides a reusable, yet still antiseptic, toothpick in a truly portable container.

Secondly, the device additionally provides antiseptic and an applicator for the antiseptic so that chemical, as well as mechanical, cleansing of the mouth may take place.

Thirdly, the operation of the toothpick is neat, easy and unobtrusive.

Having now illustrated and described my invention, it is not intended that such description limit this invention, but rather that this invention be limited only by a reasonable interpretation of the appended claims.

What is claimed is:

1. An antiseptic toothpick comprising:
   (a) a case including a base end and a top end, said case including internal wall threads;
   (b) a hollow cylinder adapted to contain a liquid and including a base end and a top end and sealed at both ends, said cylinder threadably engaged on its external wall with case internal wall to give controllable telescopic action;
   (c) a wick adapted to sealingly fit through said top end of said hollow cylinder to absorb and transmit liquid therethrough;
   (d) a toothpick fastened to the internal center of said base end of said case and extending into and through said hollow cylinder and into a portion of said wick,
   whereby, when through said telescopic action said hollow cylinder is retracted into said case, said toothpick protracts through said wick and into an exposed position and when said telescoping action is reversed, said toothpick retracts within said cylinder, leaving said wick available for use as an applicator.

2. The toothpick according to claim 1 including, additionally, antiseptic liquid located in said hollow cylinder.

3. The toothpick according to claim 1 wherein said wick of part (c) is felt.

4. The toothpick according to claim 1 including, additionally, a cap adapted to overfit said wick.

5. The toothpick according to claim 4 wherein said cap is plastic.

6. The toothpick according to claim 1 wherein said toothpick includes a tapered pin and a rod, said tapered pin connected to one of said rod's ends at the nontapered end of said pin, said rod's other end attached to said base end of said case.

7. The toothpick according to claim 1 wherein said hollow cylinder includes, at each end, gaskets as sealing means.

8. The toothpick according to claim 1 wherein said case and said hollow cylinder are plastic.

9. The toothpick according to claim 1 wherein said toothpick is plastic.

10. The toothpick according to claim 1 wherein said toothpick is hard rubber.

11. The toothpick according to claim 1 wherein said case is cylindrical.

12. The toothpick according to claim 2 wherein said liquid in said hollow cylinder includes fluoride.

* * * * *